(12) United States Patent
Park et al.

(10) Patent No.: US 8,673,653 B2
(45) Date of Patent: Mar. 18, 2014

(54) SIGNAL AMPLIFICATION TECHNIQUE FOR MASS ANALYSIS

(75) Inventors: Hyung-Soon Park, Seoul (KR); Sang-Wan So, Yongin (KR); Woon-Seok Yeo, Seoul (KR); Soo-Jae Lee, Seoul (KR); Jung-Rok Lee, Seoul (KR); Ju-Hee o Lee, Seoul (KR); Kwang-Pyo Kim, Seoul (KR)

(73) Assignee: Diatech Korea Co., Ltd., Seoul (KR)

( * ) Notice: Subject to any disclaimer, the term of this patent is extended or adjusted under 35 U.S.C. 154(b) by 566 days.

(21) Appl. No.: 12/937,139

(22) PCT Filed: Apr. 10, 2009

(86) PCT No.: PCT/KR2009/001839
§ 371 (c)(1),
(2), (4) Date: Nov. 2, 2010

(87) PCT Pub. No.: WO2009/125989
PCT Pub. Date: Oct. 15, 2009

(65) Prior Publication Data
US 2011/0053292 A1    Mar. 3, 2011

(30) Foreign Application Priority Data

Apr. 10, 2008  (KR) .................. 10-2008-0033262
Nov. 11, 2008  (KR) .................. 10-2008-0111446

(51) Int. Cl.
*G01N 33/553*    (2006.01)
(52) U.S. Cl.
CPC .................................. *G01N 33/553* (2013.01)
USPC .......... 436/525; 435/7.1; 435/7.92; 436/173; 436/518
(58) Field of Classification Search
None
See application file for complete search history.

(56) References Cited

U.S. PATENT DOCUMENTS

| | | |
|---|---|---|
| 6,197,515 B1 | 3/2001 | Bamdad et al. |
| 2005/0148101 A1* | 7/2005 | Bamdad et al. ............... 436/524 |
| 2007/0059732 A1* | 3/2007 | Bamdad et al. .................. 435/6 |

FOREIGN PATENT DOCUMENTS

KR     100737689 B1      7/2007

OTHER PUBLICATIONS

J.R Lee, et al., "Mass Spectrometry Signal Amplification Method for Attomolor Detection of Antigens Using Small-Molecule-Tagged Gold Microparticles" In Angewandte Chemie. vol. 120(49):9660-9663 (Published on line Oct. 29, 2008).
Edward T. Castellana and David H. Russell "Tailoring Nanoparticle Surface Chemistry to Enhance Laser Desorption Ionization of Peptides and Proteins" in Nano Letters. vol. 7(10:3023-3025(Publiched on line Sep. 21, 2007).
S. Hou, et al., "Inhibition of *Escherichia coli* Biofilm Formation by Self-Assembled Monolayers of Functional Alkanethiols on Gold" in Applied and Environmental Microbiology. vol. 73(13):4300-4307 (Published online May 4, 2007).
Z.J. Zhu, et al. "Multiplexed Screening of Cellular Uptake of Gold Nanoparticles Using Laser Desorption/Ionization Mass Spectrometry" in J. Am. Chem Soc. vol. 130(43):14139-14143 (Oct. 29, 2008).

* cited by examiner

*Primary Examiner* — Gary W Counts
(74) *Attorney, Agent, or Firm* — Edwards Wildman Palmer LLP

(57) ABSTRACT

Provided is a novel method for amplifying mass spectrometric signals. A novel method for detecting signals of a target molecule includes: allowing a sample, which comprises a target molecule, to contact a gold particle having a surface modified to selectively bind the target molecule, allowing a low molecular weight molecule engrafted to the gold particle generate mass spectrometric signals after the interaction, e.g., binding, between the gold particle and the target molecule, and amplifying the mass spectrometric signals to generate much mass spectrometric signals of the low molecular weight molecule even when trace amounts of the target molecule are present. An assay system using the method and the gold particle prepared in the method are provided. The method amplifies signals of the target molecule without pretreatment of a sample, making it possible to measure the target molecule simply and precisely.

12 Claims, 9 Drawing Sheets

SIGNAL AMPLIFICATION TECHNIQUE FOR MASS ANALYSIS

CROSS-REFERENCES TO RELATED APPLICATIONS

This application is a U.S. national phase application, pursuant to 35 U.S.C. §371 of PCT/KR2009/001839, filed Apr. 10, 2009, designating the United States, which claims priority to Korean Application No. 10-2008-0033262, filed Apr. 10, 2008, which claims priority to Korean Application No. 10-2008-0111446, filed on Nov. 11, 2008. The entire contents of the aforementioned patent applications are incorporated herein by this reference.

TECHNICAL FIELD

The present invention relates to the detection of target molecules using mass spectrometry, and more particularly to a novel method for amplifying mass spectrometric signals capable of detecting a target molecule such as biomolecules using a gold particle whose surface is modified by low molecular organic compounds.

BACKGROUND ART

The world is turning into an aging society as the birth rate of the human population has decreased with the increased the average life span. Meanwhile, it is more important to accurately diagnose and effectively prevent and treat complicated disorders such as adult diseases and chronic diseases since fat as the human population suffering from obesity and adult diseases increases. Since a biomolecule, that is, a biomarker, which is an important factor used to diagnose disorders is generally present at a very low concentration in the human body or a test sample, there is a need for methods for detecting the biomolecule with ultrahigh sensitivity. Many measurement methods known up to now have excellent sensitivity, but have the following problems which are short of performance or should be improved further:

(1) Are they used as a method for amplifying biological signals which may be generally used in the art, as well as signals of certain disorders, certain test samples, etc.?

(2) Are they easily used in experimental methods?

(3) It is easy to avoid the amplification of false signals caused by the non-selective absorption?

(4) Is there no problem in aspect of the costs used to perform a large number of experiments?

These factors are important in precisely analyzing a limited amount of a test sample and accurately diagnosing the assay results. Therefore, in order to overcome the difficulty in the existing analytic methods such ELISA, in which one marker molecule should be analyzed one by one, there is increasing demand for the development of measurement methods which may be used to compare and analyze various marker molecules for diseases at a time.

Mass spectrometry is a method in which biomolecules such as nucleic acids, proteins, peptides and sugars may be used to accurately determine the kind and amount of a common organic compound to be analyzed by measuring the molecular weight and signal intensity of the target molecule. In theory, the mass spectrometry has a broad range of available molecules since it is used without regard to the presence of certain functional groups. Also since the mass spectrometry may often be used to exactly analyze various kinds of target molecules in a complicated test sample at a time, it is, for example, possible to analyze and diagnose various disease marker molecules.

Several kinds of the mass spectrometry are present according to the ionization of a test sample and the detection of ions. Among them, matrix-assisted laser desorption/ionization-time-of-flight (MALDI-TOF) mass spectrometry has been widely used for the mass spectrometry of test biosamples. The MALDI-TOF mass spectrometry has been known as a method most suitable for ultrahigh-throughput diagnosis in which a large number of test samples should be diagnosed rapidly. However, the MALDI-TOF mass spectrometry has a problem in that when it is used to directly measure a molecular weight of a target molecule, its sensitivity is very deteriorated, which makes it difficult to measure a small amount of a biomarker. Also, it is difficult to obtain information on the presence of a biomarker and an amount of the biomarker using the MALDI-TOF mass spectrometry. Therefore, in order to solve the above-mentioned problems, the development of high-sensitive quantitative MALDI-TOF mass spectrometry, and the further development of signal-amplifiable mass spectrometry which can be used to quantitatively analyze a trace of biomolecule are absolutely required.

DISCLOSURE

Technical Problem

Accordingly, the present invention is designed to solve the problems of the prior art, and therefore it is an object of the present invention to provide a system and method capable of releasing mass spectrometric signals which are generated from one target molecule and amplified with magnifications of several thousands to several ten thousands.

Technical Solution

According to an aspect of the present invention, there is provided a gold particle for capturing a target molecule whose surface is engrafted with a low molecular molecule for generating signals and amplifying signals, an assay system using the gold particle, and a method for analyzing a target molecule using the gold particle and the assay system.

In one aspect of the present invention, the gold particle may include a signal generator, a linker and a capturing molecule. A plurality of the signal generators may be connected to the surface of the gold particle having a self assembled monolayer formed in the surface thereof. One end of the linker may be bound to the surface of the gold particle, and the other end of the linker may be connected to a capturing molecule which is bound specifically to a target molecule, or specifically reacts to the target molecule. Here, the signal generator may be an organic compound which is extricated from the gold nanoparticle in the mass spectrometry of the gold particle to form a plurality of organic cations having a different molecular weight than the target molecule.

According to one exemplary embodiment of the present invention, the signal generator may include an ether terminus formed at one terminus thereof and bound to the surface of the gold particle via a gold-sulfur (Au—S) bond; and an alkanethiol portion formed at one terminus thereof and bound to the surface of the gold particle. Here, the ether terminus may include at least one ethylene glycol unit. According to one exemplary embodiment of the present invention, the gold particle may generate mass signals of the signal generator using laser desorption ionization-time of flight (LDI-TOF) mass spectrometry.

According to another aspect of the present invention, there is provided an assay system including the gold particle and a target immobilizing matrix capable of immobilizing the gold particle and a test sample to be analyzed on the surface of a support. In this case, the target immobilizing matrix may be provided with a solid support, and thus may immobilize a test sample on the surface of the support via a covalent bond or a non-covalent bond, where the test sample may be used to determine whether the target molecule is present in the surface of the support. According to one exemplary embodiment of the present invention, the target immobilizing matrix may include a plurality of signal generators coupled to the surface of the target immobilizing matrix via Au—S bond, the target immobilizing matrix having a self assembled monolayer formed on the surface thereof; at least one linker coupled to the surface of the target immobilizing matrix; and a capturing molecule coupled to the linker to immobilize the target molecule via a covalent bond or a non-covalent bond. In this case, the signal generators may be organic compounds which are released from the gold nanoparticle in the mass spectrometry of the gold particle to form a plurality of organic cations having a different molecular weight than the target molecule and the signal generators of the gold particle.

According to still another aspect of the present invention, there is provided a method for analyzing a target molecule in a test sample using the gold particle. The method may include: generating a capturing mixture by allowing a capturing molecule immobilizing matrix, in which the capturing molecule binding to the target molecule is immobilized on the surface of a solid support, to be in contact with the above-mentioned gold particle and a test sample in which it is required to determine whether or not a target molecule is present; screening the capturing mixture by removing a non-specifically bound gold particle from the capturing mixture; and subjecting the gold particle remaining in the capturing mixture after the screening step to mass spectrometry. In this case, the mass spectrometry used to analyze the capturing mixture may be matrix-free laser desorption ionization mass spectrometry or conventional MALDI-TOF mass spectrometry. Also in a step between the steps of screening the capturing mixture and subjecting the gold particle to mass spectrometry, the bound gold particle may be isolated from the capturing mixture, and subjected to the mass spectrometry.

Advantageous Effects

The system and method for amplifying mass spectrometric signals according to the present invention may be useful to specifically amplify mass spectrometric signals of the target molecule to be analyzed without any pretreatment of a test sample and quantitatively measure the target molecule without any interference of other compounds.

DESCRIPTION OF DRAWINGS

These and other features, aspects, and advantages of preferred embodiments of the present invention will be more fully described in the following detailed description, taken accompanying drawings. In the drawings:

FIG. 1 shows an assay procedure of a mass spectrometry system in which AM-mass tags are used as signal generators.

FIG. 2 shows formulas of AM-mass tag molecules which may be immobilized on the surface of a gold particle via a sulfur-gold (S—Au) bond.

FIG. 3 shows that a capturing molecule is not bound to AM-mass tag 2 that functions as a linker.

FIGS. 6(A) and 6(C) show the analysis results of a biotin target immobilizing matrix, and FIGS. 6(B) and 6(D) show the analysis results of a glutathione (GSH) target immobilizing matrix. Here, the percentage (%) in the graph represents a fixed density of the target molecule present in the surface of the target immobilizing matrix.

FIG. 7(A) is a mass spectrum graph obtained by the reaction between a target immobilizing matrix on which a biotin target molecule is immobilized and a gold particle having a neutravidin capturing molecule, FIG. 7(B) is a mass spectrum graph obtained by the reaction between a target immobilizing matrix on which a biotin target molecule is immobilized and a gold particle having a myoglobin capturing molecule, and FIG. 7(C) is a mass spectrum graph obtained by the reaction between a biotin-free target immobilizing matrix and a gold particle having a neutravidin capturing molecule.

FIG. 8(A) is a mass spectrum graph obtained by analyzing a SAM gold plate having SMAs of AM-mass tag 1 shown in FIG. 2 using MALDI-TOF mass spectrometry, 8(B) is a mass spectrum graph obtained by analyzing the same SAM gold plate using matrix-free laser desorption ionization mass spectrometry, and 8(C) is a mass spectrum graph obtained by allowing the same SAM gold plate to react to a gold particle having SMAs of AM-mass tag 5.

BEST MODE

Figure 1:
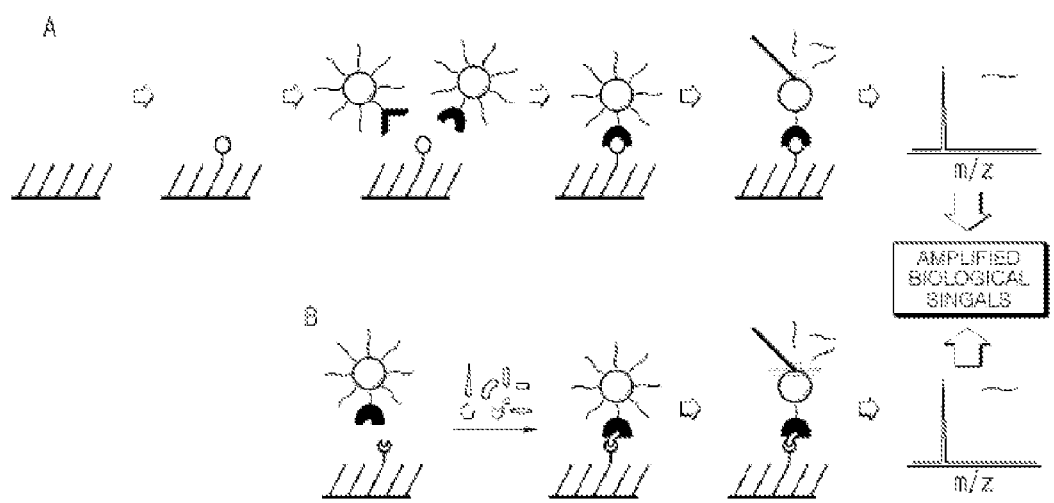
FIG. 1 is a principle of amplifying mass spectrometric signals according to one specific embodiment of the present invention. Here.

Hereinafter, preferred embodiments of the present invention will be described in detail referring to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

The main technology to be realized in the present invention is a novel method for amplifying signals in which one target molecule may be used to detect a large number of low molecular molecules, the method including: modifying the surface of a gold particle so that the gold particle can selectively bind to the target molecule and detecting the low molecular molecules, which are engrafted to the gold particle by their interaction with the target molecule, using mass spectrometry.

In order to capture the target molecule and amplify the signals according to the present invention, the surface of the gold particle is modified with an organic compound, and engrafted to the low molecular organic compound. This surface-modified gold particle has a signal generator, a linker and a capturing molecule. In the gold particle of the present invention, the capturing molecule is a portion that specifically binds to the target molecule, and one end of the linker is coupled to the capturing molecule and the other end is coupled to the gold particle. Meanwhile, the signal generator is an organic compound that is bound in the plural number to the surface of the gold particle to amplify the signals, and extricated from the gold nanoparticles in the mass spectrometry of the gold particle to form a plurality of organic cations having a different molecular weight than the target molecule. According to the present invention, the organic compound constituting the signal generator is used to form a self assembled monolayer (SAM). The formation of the self assembled monolayer makes it possible to detect mass spectrometric signal without any matrix formation, as described below. Also, the formation of SAM makes it easier to stably connect the biological marker to the gold particle.

The gold particle of the present invention includes a highly larger number of signal generators than the capturing molecules. Even when only one target molecule in a very small amount of a test sample or a trace of a test sample captures one target molecule, the assay sensitivity of the gold particle may be enhanced in the mass spectrometry by detecting secondary mass spectrometric signals which are amplified by a large number of signal generator molecules or their fragments generated from the gold particle.

FIG. 1 is a diagram showing a principle of amplifying signals using a signal generator as a mass tag according to some exemplary embodiments of the present invention. FIG. 1A is one aspect of detecting a target molecule using the gold particle of present invention to capture the target molecule and amplify the signals. The last schematic view of FIG. 1A shows a solid support having a surface on which the target molecule may be immobilized. The target molecule (open circle) is previously immobilized on the solid support (the second schematic view from the left of FIG. 1A), and various kinds of the gold particle according to the present invention are applied to the target molecule (the third schematic view from the left. The gold particle of the present invention is shown in the form of a large ball having meandering projections, as shown in FIG. 1. In this schematic view, the projections radially attached to the ball represent signal generators, a darkened half-moon or V-shaped molecule represents a capturing molecule, and a molecule connecting the capturing molecule to an open large ball represents a linker. Only the gold particle that specifically bind to the target molecule may be screened and maintained intact (the fourth schematic view from the left of FIG. 1A). Then, the signal generators are isolated from the screen gold particle in the mass spectrometry using an ionization laser (the fifth schematic view from the left) to emit mass spectrometric signals (the last schematic view of FIG. 1A).

Meanwhile, in FIG. 1B showing another exemplary embodiment of the present invention, the target molecule does not undergo the immobilizing pretreatment as shown in FIG. 1A. As shown in FIG. 1B, the gold particle, a solid support and a non-immobilize target molecule sample are mixed and incubated and there is no pretreatment of the target molecule (the leftmost schematic view of FIG. 1B). A test sample containing the target molecule and the other molecules is added to the gold particle and screened to obtain a complex of the gold particle, the target molecule and the support (the second schematic view from the left). Then, the gold particle-target molecule-support complex undergoes the procedures as shown in FIG. 1A to emit mass spectrometric signals.

The size of the gold particle of the present invention may be selected according to their uses, but the present invention is not particularly limited thereto. That is to say, the gold particle may be nanometer-sized nanoparticles, or micrometer-sized microparticles. For example, the nanoparticles may be desirable to determine a structure of an object having a fine surface structure such as cell surfaces, and the microparticles are advantageous in that they have high stability in a colloidal coloidal state and their surfaces are easy to modify. Also, the microparticles have an advantage in that the positive amplification of signals is observed since a large number of signal generators are bound to the surface of one gold particle.

The target molecule analyzed with the gold particle and the capturing molecule for specifically capturing target molecule may be used in the present invention without any particular limitation. The capturing molecules and the target molecules that may be captured via a specific interaction, for example, a hydrogen bond, or captured by a highly selective chemical reaction may be used in the present invention. Therefore, all the organic compounds, inorganic compounds, biomolecules and macromolecules that satisfy the above-mentioned requirements may be used as the target molecule. For example, biotin, avidin, small ligands and protein receptors target small organic compounds as a target molecule, and the capturing molecule may be a protein that specifically binds to the small organic compounds. Of course, it is possible to use a protein as the target molecule and a small organic compound as the capturing molecule. Like crown ether or cryptand and cations that specifically bind to the crown ether or cryptand, the target molecule may be an inorganic ion, and the capturing molecule may be an organic compound. Also, like an enzyme and its irreversible inhibitor (for example, an organic phosphorus compound such as sarin and acetylcholinesterase), the capturing molecule and the target molecule may be connected to each other via a covalent bond by means of the specific chemical reaction between them.

Since there are various examples of the biomolecules having specific binding characteristics, the biomolecules may be desirably used as the target molecule of the present invention. Among them, nearly all of the biomolecules, for example, proteins, peptides, nucleic acids, carbohydrates, lipids, carbohydrate-protein conjugates, lipid-protein conjugates may be sued as the target molecule. The signal generator of the present invention is not a macromolecule but an organic compound that is used to form a self assembled monolayer (SAM). Since molecules forming SAM may be prepared with a wide range of length and prepared from various chemical compounds, it is possible to prepare and classify various SAM-forming molecules having different molecular weight according to various biological target molecules. In the present invention, the SAM-forming molecules used to amplify signals are referred to as an amplifying mass tag (or, commonly abbreviated to "AM-mass tag").

Figure 2:
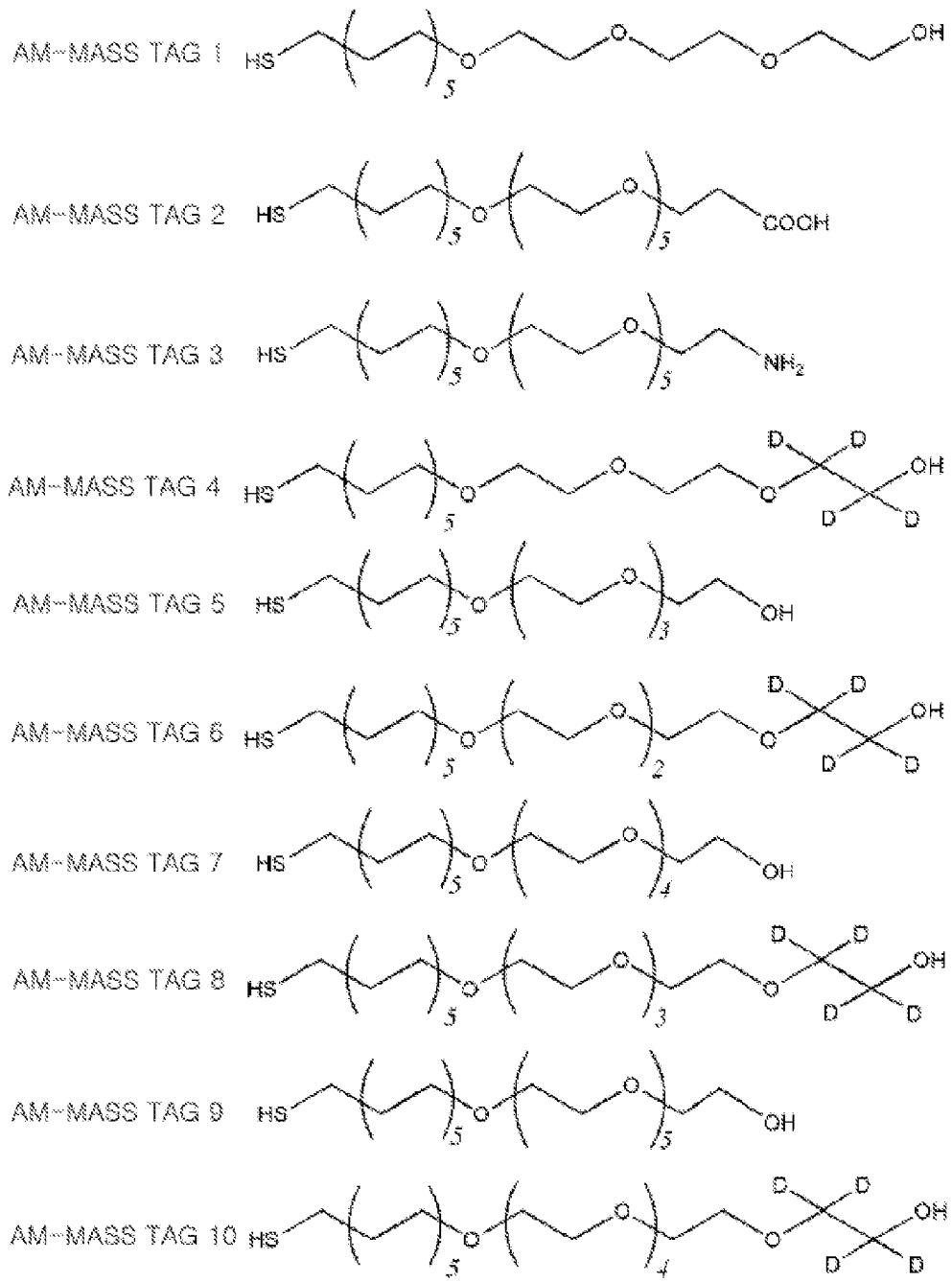
FIG. 2 is one specific embodiment of a signal generator which may be used as a gold particle according to the present invention or a target immobilizing matrix. Here.

According to one exemplary embodiment of the present invention, the signal generator has an alkanethiol portion formed in one terminus thereof, the alkanethiol portion being coupled to the surface of the gold particle via a gold-sulfur (Au—S) bond, and has an ether terminus formed opposite to the alkanethiol portion. According to one further specific embodiment of the present invention, the ether terminus preferably has at least one ethylene glycol repeating unit. The ether terminus having the ethylene glycol repeating unit may be used to prevent the non-specific absorption of proteins. Examples of the AM-mass tag molecules having such an ethylene glycol repeating unit are shown in FIG. 2. The AM-mass tags according to one exemplary embodiment of the present invention (including the AM-mass tag molecules as shown in FIG. 2) are easily separated from the gold particle in the laser desorption ionization mass spectrometry such as MALDI-TOF mass spectrometry to generate mass spectrometric signals.

According to the present invention, the gold particle having different capturing molecules and different AM-mass tags may match the respective target molecules, as shown in FIGS. 1 and 2. Various target molecules may be subjected to multiplex assay at a time using a plurality of the gold particle. The mass spectrometry is suitable for the multiplex assay since it is used to easily measure a fine difference in molecular weight.

Another aspect of the present invention is to provide a system for analyzing a target molecule, including the gold particle. This assay system is configured to include a target immobilizing matrix that is able to immobilize the gold particle and a test sample to be analyzed on the surface of a support. In this case, the target immobilizing matrix may be provided with a solid support to immobilize a test sample, which is analyzed to determine the presence of the target molecule, on the support surface via a covalent bond or a non-covalent bond. For such an assay system, the test sample may be used after the immobilization on the target immobilizing matrix as shown in FIG. 1A, or be used without any immobilizing pretreatment as shown in FIG. 1B. In the assay system according to one exemplary embodiment of the present invention, the target immobilizing matrix is configured to have an immobilization unit for immobilizing a target molecule on a solid support. For this purpose, the surface of the support may be modified. The immobilization unit for immobilizing a target molecule is preferably peculiar, but if immobilization units may be configured so that the capturing molecule of the gold particle according to the present invention can specifically bind to the target molecule, they may be used without any limitation. The immobilization of the target molecule on the surface of the support of the target immobilizing matrix may be performed without any limitation using either a method for forming a covalent bond between the target molecule and the surface or modified surface of the support or a method for immobilizing the target molecule one the surface or modified surface of the support via a non-covalent bond (for example, a bond such using an intermolecular force, such as hydrogen bond).

In the assay system according to one exemplary embodiment of the present invention, conventional materials such as glass, silicon, metals, semiconductors or plastics may be used as the support of the target immobilizing matrix. According to any specific embodiment, the target immobilizing matrix may be a biochip on which other biomolecules obtained from a certain test biosample, as well as the target molecule, are immobilized. For example, the target immobilizing matrix may be a biochip in which proteins in a cell lysate sample obtained from cells of a certain stage are immobilized on the surface of a support via a non-specific covalent bond.

According to one exemplary embodiment of the present invention, like the gold particle, the target immobilizing matrix may be configured to include a self assembled monolayer formed of low molecular organic compounds and a capturing molecule. That is to say, the target immobilizing matrix may include a plurality of signal generators coupled to the surface of the target immobilizing matrix via a gold-sulfur (Au—S) bond, the target immobilizing matrix having a self assembled monolayer (SAM) formed in the surface thereof; at least one linker coupled to the surface of the target immobilizing matrix; and a capturing molecule coupled to the linker to immobilize the target molecule via a covalent bond or a non-covalent bond. In this case, the signal generators may be organic compounds (AM-mass tags) which are extricated from the gold nanoparticles in the mass spectrometry of the gold particle to form a plurality of organic cations having a different molecular weight than the target molecule and the signal generators of the gold particle. According to one further specific embodiment of the present invention, the gold particle and the target immobilizing matrix are provided with a monolayer of the signal generators having an alkanethiol portion and an ethylene glycol repeating unit. Here, the signal generators are formed of different molecules, namely AM molecules, and different antibodies that specifically bind to the same target molecule are used as the capturing molecule.

According to another aspect of the present invention, a method for analyzing a target molecule in a test sample using the target immobilizing matrix and the gold particle is provided. The method including the pretreatment of the test sample as shown in FIG. 1A is configured to include the following steps:

(i) obtaining a target immobilizing matrix in which a test sample is in contact with a solid support to immobilize components (a target molecule or other compounds) in the test sample on the surface of the solid support;

(ii) generating a capturing mixture by allowing the target immobilizing matrix to be in contact with the gold particle defined in any one of claims 1 to 8 under the condition where a capturing molecule connected to the gold particle of the present invention specifically binds to the target molecule;

(iii) screening the capturing mixture by removing a non-specifically bound gold particle from the capturing mixture; and (iv) subjecting the gold particle remaining in the capturing mixture after Step (iii) to mass spectrometry.

The method for binding a gold particle and a test sample to a target immobilizing matrix at a time without any immobilization of the test sample on the target immobilizing matrix includes the following steps:

(i) generating a capturing mixture by allowing the test sample and the gold particle defined in any one of claims 1 to 8 to be in contact with a capturing molecule immobilizing matrix in which the capturing molecule bound to the target molecule is immobilized on the surface of the solid support;

(ii) screening the capturing mixture by removing a non-specifically bound gold particle from the capturing mixture; and (iii) subjecting the gold particle remaining in the capturing mixture after Step (ii) to mass spectrometry.

Since the mass spectrometry of the target molecule according to the present invention uses the amplification of signals, it has an advantage in that it may quantify the target molecule using its high sensitivity and the intensity of secondary signals of the signal generators measured in a mass spectrometer. A method using an internal standard of a known amount and a gold particle corresponding to the internal standard may be used for the purpose of the quantitative analysis. The method for analyzing a target molecule according to one exemplary embodiment of the present invention has an advantage in that the capturing mixture in which the target immobilizing matrix is bound to the gold particle by the components of the test sample, particularly a capturing mixture which is screened by removing the gold particle non-specifically bound to the target immobilizing matrix, may be used without any other treatments. The signal generator, for example an AM-mass tag, according to one exemplary embodiment of the present invention is directly isolated from the capturing mixture using laser desorption ionization mass spectrometry to takes place of cations that generate mass spectrometric signals. As the conventional laser desorption ionization mass spectrometry, a matrix-assisted laser desorption ionization (MALDI) mass spectrometry is used, which includes: mixing a matrix-forming agent and a test sample to form a matrix and desorbing and ionizing a target compound to be analyzed by irradiating the matrix with a laser. However, since the assay method according to one exemplary embodiment of the present invention has a merit in that unnecessary procedures may be omitted since the screened capturing mixture may be directly introduced into a laser desorption ionization mass spectrometer without any formation of the matrix. Although it was previously described that the gold particle according to one exemplary embodiment of the present invention is subjected to the multiplex assay, the gold particle may be directly subjected to the mass spectrometry without any additional treatment of the test sample after the test sample undergoes the minimum screening process. Therefore, the assay method according to one exemplary embodiment of the present invention is also suitable for a high-throughput assay. Meanwhile, the assay method according to one exemplary embodiment of the present invention may further include: analyzing the capturing mixture using the conventional MALDI-TOF mass spectrometry, that is, forming a matrix on the capturing mixture before the mass spectrometry of the gold particle.

In the assay method according to one exemplary embodiment of the present invention, the mass spectrometry used herein may include all of the mass spectrometries in which the signal generators may be extricated from the gold particle in the mass spectrometer, but the present invention is not particularly limited thereto. Among them, the laser desorption ionization mass spectrometry may be used to easily generate mass spectrometric signals from the gold particle of the present invention as described above, and is particularly suitable for the ionization of the biomolecule sample. MALDI-TOF mass spectrometry is most widely used as the laser desorption ionization mass spectrometry. Commercially available mass spectrometers generally use a combination of the MALDI ionization and TOF ion detection systems, but the present invention is limited to the TOF detection system. Also, the assay method of the present invention may further include: isolating only the specifically bound gold particle or bound gold particle-test sample from the screened capturing mixture before the mass spectrometry of the gold particle. When it is possible to isolate only the gold particle, the present invention may be applied to ionization mass spectrometers other than the laser desorption ionization mass spectrometry.

The conventional MALDI-TOF mass spectrometry has a detection limit of several picomoles, but the mass spectrometry using the signal amplification proposed in the present invention may be used to detect a trace (less than $10^{-15}$ attomole) of the test sample.

MODE FOR INVENTION

Hereinafter, exemplary embodiment of the present invention will be now described in more detail. However, it should be understood that examples and synthetic examples are given by way of illustration only, since various changes and modifications are made within the scope of the invention without departing from the spirit and scope of the invention.

Example 1

Synthesis of AM Molecule

Step 1: Synthesis of AM-Mass Tag

AM-mass tags having different molecular weights as shown in FIG. 2 were synthesized by binding ethylene glycol repeating units of various lengths to long-chain thiol having a long alkyl group.

Example 2

Preparation of Gold Particle Having Capturing Molecule

A gold particle having a capturing molecule was prepared according to one specific embodiment of the present invention. The gold particle has a structure in which a linker and the capturing molecule are present within a self assembled monolayer (SAM) composed of AM-mass tags. 4 kinds of the gold particle was prepared as listed in the following Table 1.

TABLE 1

| No. | Target Molecule | Capturing molecule |
|---|---|---|
| Gold particle 1 | Glutathione (GSH) | Glutathione-S-Transferase (GST) |
| Gold particle 2 | Biotin | Neutravidin |
| Gold particle 3 | α-Fetoprotein (AFP) | AFP-Specific Polyclonal Antibody |
| Gold particle 4 | Adiponectin | Adiponectin-Specific Monoclonal Antibody 1 |
| Gold particle 5 | — | Myoglobin | ab8201 from Abcam® (U.K.) was used as an α-fetoprotein (AFP) polyclonal antibody, and ab3980 was used as a monoclonal antibody. MAB 1065 (R&D Systems, USA) was used as an adiponectin polyclonal antibody, and MAB10651 was used as a monoclonal antibody.

Figure 3:
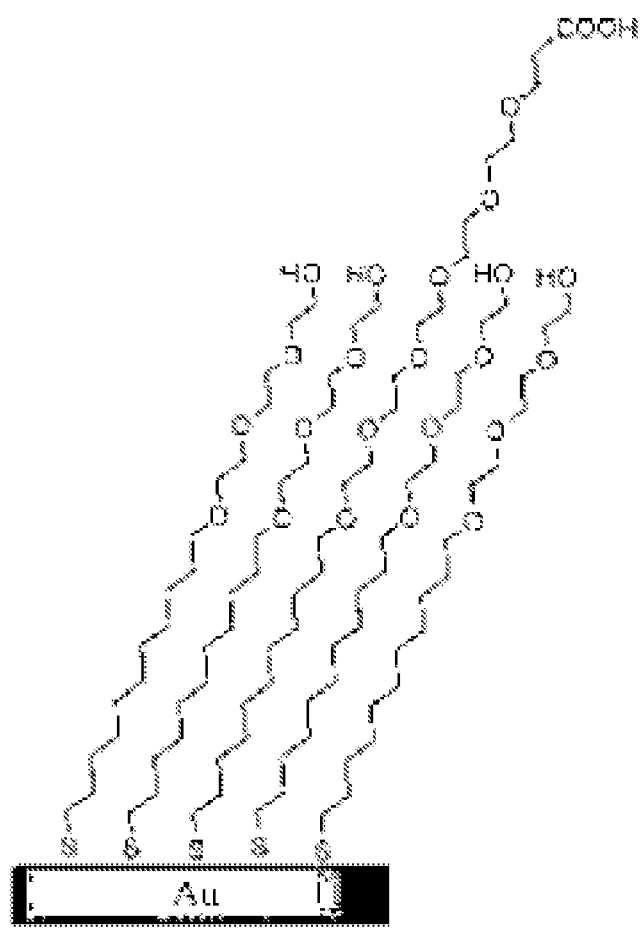
FIG. 3 is a diagram showing a complex molecule in which AM-mass tag 1 and AM-mass tag 2 shown in FIG. 2 are used to form a self assembled monolayer (SAM) on the surface of the gold particle or the target immobilizing matrix. Here.

The signal generators of the gold particle were prepared by binding AM-mass tag 1 shown in FIG. 2 to a gold particle via a sulfur-gold bond, and the linker was also prepared by binding AM-mass tag 2 shown in FIG. 2 to a gold particle via a sulfur-gold bond. FIG. 3 shows a complex molecule in which a self assembled monolayer (SAM) of AM-mass tag 1 is formed before the binding of the capturing molecule protein to the linker. Here, the finished gold particle serves to connect an amino group of the capturing molecule protein to the carboxyl terminus of AM-mass tag 2 via a peptide bond. In this case, the carboxyl terminus of AM-mass tag 2 serves as the linker.

Step 1: Formation of Self Assembled Monolayer (SAM) on Surface of Gold Particle

①  1 mg of gold particle (Nomadien Corporation, Korea) having an average diameter of 2 nm was washed with absolute ethanol and centrifuged for 2 minutes, and a supernatant was then removed off. This procedure was repeated three times.

②  the gold particle suspension was sonicated for 5 minutes, washed with absolute ethanol and centrifuged for 2 minutes, and a supernatant was then removed off. This procedure was repeated three times.

③  a 1 mM absolute ethanol solution containing AM-mass tag 1 (serving as a signal generator) shown in FIG. 2 and a 1 mM absolute ethanol solution containing AM-mass tag 2 (serving as a signal generator) were mixed in a volume ratio of 1:99.

④  1 mL of the mixed solution prepared in Substep ① was mixed with the gold particle prepared in Substep ② and reacted in a dark room for a day (approximately 12 hours or more) using a rotator.

⑤  the reaction mixture was centrifuged for 5 minutes, and a supernatant was then removed off.

⑥  1 mL of absolute ethanol was mixed with a pallet of the reaction mixture, and centrifuged for 3 minutes, and a supernatant was then removed off. This procedure was repeated five times. Then, the resulting mixture pallet was dissolved in absolute ethanol and stored at −20° C.

Figure 4:
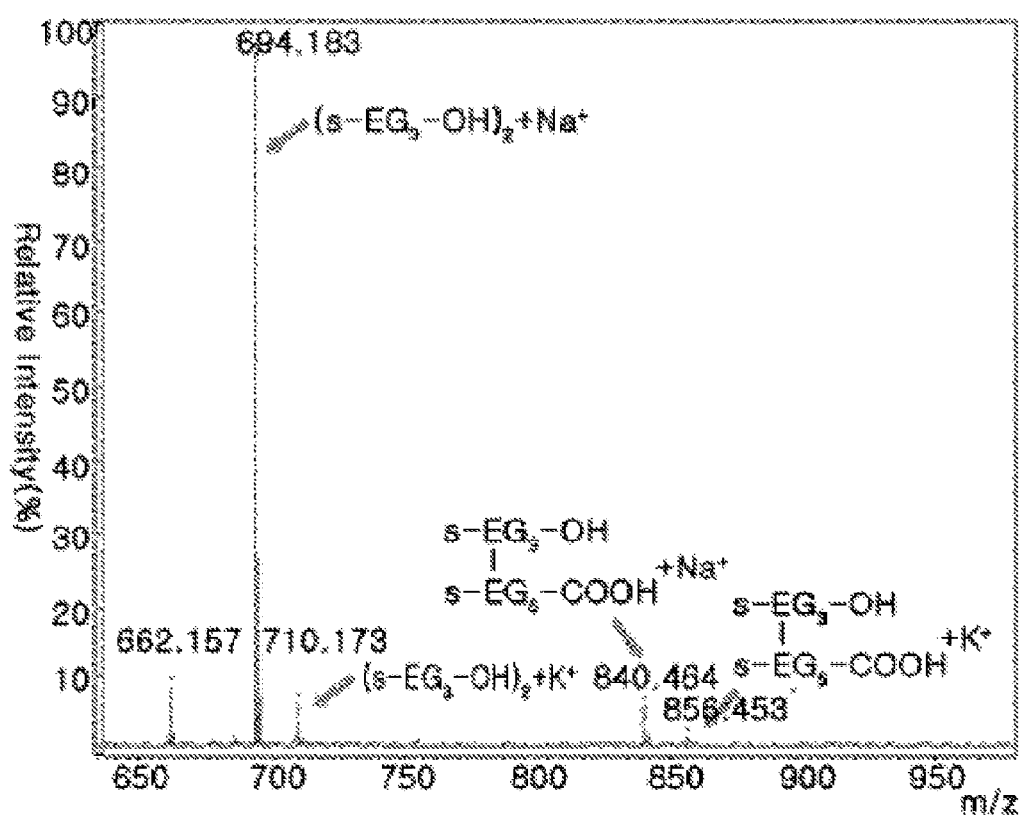
FIG. 4 is a mass spectrum graph showing that AM-mass tag 1 and AM-mass tag 2 are bound to the surface of the gold particle as described in Example 2 to determine whether or not SAMs are formed on the capturing molecule-free gold particle.

FIG. 4 is a MALDI-TOF mass spectrum graph determining whether or not a self assembled monolayer (SAM) of AM-mass tag 1 is formed on the surface of the gold particle. The mass spectrometry of FIG. 4 was performed using DHB as a matrix as described below in Example 8. The highest peak (m/z=694.183) represented by $(s-EG_3-OH)_2+Na^+$ in the mass spectrometry of FIG. 4 indicates a peak of an ion species in which sodium ions are bound to a molecule in which disulfide (S—S bond) is formed in an alkanethiol portion of AM-mass tag 1. In addition, bridged ions of AM-mass tags 2 and 1 were also observed in FIG. 4, and the mass spectrum exactly coincides with the fact that a main chemical species, SAM, of AM-mass tag 1 is formed on the surface of the gold particle.

Step 2: Binding of Capturing Molecule to Gold Particle

The 5 capturing molecule proteins listed in Table 1 were bound to the COOH terminus of AM-mass tag 2 which was bound via a peptide bond to the surface of the gold particle obtained Step 1.

①  A gold particle having a monolayer of 1% AM-mass tag 2 and 99% AM-mass tag 1 formed therein was transferred to a PCR tube and centrifuged, and a supernatant was then removed off.

②  100 μL of methylene chloride was mixed and centrifuged (5000×g, 5 minutes), and a supernatant was then removed off. This procedure was repeated three times.

③  50 μL of an N-hydroxysuccinimide (NHS) solution (5 mg/mL in methylene chloride) was mixed with the centrifuged gold particle, and reacted for 3 minutes.

④  20 μL of a 1-ethyl-3-(3-dimethylaminopropyl)carbodiimde (EDC) solution (20 mg/mL in methylene chloride) was mixed with the resulting reaction mixture, and reacted at a room temperature for 2 hours.

⑤  A centrifuge was used (5000×g, 5 minutes) to remove off a supernatant.

⑥  100 μL of methylene chloride was mixed with the gold particle, and centrifuged (5000×g, 5 minutes) to remove off a supernatant. This procedure was repeated five times.

⑦  10 μL of PBS solution including the capturing molecule protein bound to the linker was added at a content of 50 μL to the gold particle, mixed and reacted at a room temperature for 1 hour. The capturing molecule proteins were GST, myoglobin (Sigma-Aldrich®, USA), neutravidin (Pierce Biotech, USA), AFP-specific monoclonal antibody and polyclonal antibody (Abcam®, U.K.), and adiponectin-specific monoclonal antibody 1 (R&D Systems®, USA), respectively.

⑧  The resulting reaction mixture was centrifuged (5000× g, 5 minutes) to remove off a supernatant.

⑨  PBS was mixed with the gold particle, and the resulting mixture was centrifuged (5000×g, 5 minutes) to remove off a supernatant. After this procedure was repeated twice, the resulting mixture pallet was transferred to a tube.

⑩  The mixture pallet was dissolved in absolute ethanol to form a finished gold particle, which was stored at −20° C. for the future use.

Example 3

Preparation of Target Immobilizing Matrix on which a Capturing Molecule has been Previously Immobilized A target immobilizing matrix on which a biotin or glutathione target molecule is immobilized via a chemical bond was prepared.

Preparation of Target Immobilizing Matrix to which a Glutathione Target Molecule is Captured ①  A gold-coated plate was prepared by vacuum-depositing titanium (100 Å) on the surface of a silicon wafer and stacking gold (900 Å) on the vacuum-deposited titanium layer. The gold-coated plate was cut into a suitable size, for example 5×5 mm, of pieces.

②  1 mM absolute ethanol solution of AM-mass tag 1 and a 1 mM absolute ethanol solution of AM-mass tag 3 shown in FIG. 2 were mixed at a desired volume ratio (approximately from 90:10 to 99.9999999:0.0000001).

③  The gold-coated plate was soaked into the ethanol solution prepared in Substep ②, and reacted overnight in a dark room to form a self assembled monolayer (SAM).

④  The SAM gold plate prepared thus was spray-washed with absolute ethanol, and dried with nitrogen (N2) gas.

⑤  A solution in which DMSO and PBS were mixed at a ratio of 1:1 (v/v) was used to prepare a 50 mM N-succinimidyl 3-maleimidopropinate solution.

⑥  10 μL of the 50 mM N-succinimidyl 3-maleimidopropinate solution was placed on the SAM gold plate, and reaction at a room temperature for 4 hours to prepare a maleimide SAM gold plate.

⑦  The maleimide SAM gold plate was softly washed with a DMSO/PBS (1:1) solution.

⑧  The maleimide SAM gold plate was spray-washed with absolute ethanol, and dried on $N_2$ gas.

⑨  10 μL of 50 mM glutathione (PBS solution) was placed on the maleimide SAM gold plate, and reacted at a room temperature for 2 hours to prepare a GSH SAM gold plate.

⑩  The resulting GSH SAM gold plate was softly washed with PBS.

⑪  The GSH SAM gold plate was spray-washed with absolute ethanol, and dried on $N_2$ gas.

Figure 5:
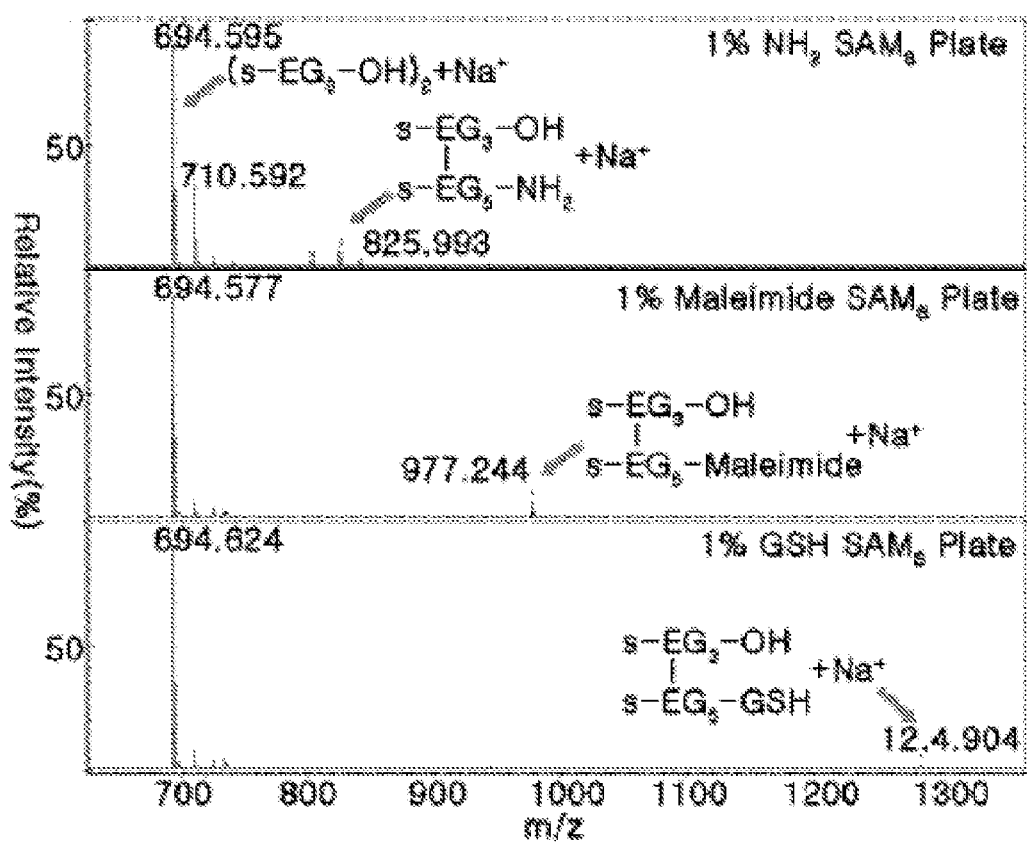
FIG. 5 is a MALDI-TOF spectrum graph showing that SAMs are formed on the surface of the target immobilizing matrix on which a glutathione target molecule is immobilized.

The mass spectrum graph as shown in FIG. 5 shows, in order, the MALDI-TOF mass spectrometry results on the SAM gold plate (1% $NH_2$ SAM gold plate), the maleimide SAM gold plate (1% maleimide SAM gold plate) and the GSH SAM gold plate prepared in Substep ④, which show that SAM is formed on the surface of the gold. Like the results shown in FIG. 4, a disulfide bond, $(s-EG_3-OH)_2+Na+ion$, between two AM-mass tag 1 molecules was observed in the SAM gold plate prepared in Substep ④. A disulfide bond, $(s-EG_3-OH)-(s-EG_5-maleimide)+Na^+$ ion, between AM-mass tag 1 and a molecule in which molecule is bound to AM-mass tag 3 was observed in the 1% maleimide SAM gold plate. A disulfide bond, (s-EG₃-OH)-(s-EG₅-GSH)+Na⁺ ion, between AM-mass tag 1 and AM-mass tag 3 to which the biotin target molecule is finally bound was observed in the 1% GSH SAM gold plate.

Preparation of Target Immobilizing Matrix to which a Biotin Target Molecule is Captured A biotin target immobilizing matrix was prepared in the same manner as in the glutathione target immobilizing matrix, except that 10 μL of a 50 mM sulfosuccinimidyl-6-(biotinamido)hexanoate PBS solution was used instead of the N-succinimidyl 3-maleimidopropinate.

Example 4

Mass Spectrometric Analysis of Target Immobilizing Matrix on which Target Molecule is Immobilized The gold particle (gold particle 1 in Table 1) with the GST capturing molecule prepared in Example 2 was used to analyze the target immobilizing matrix on which the GSH target molecule was immobilized as prepared in Example 3, and the gold particle (gold particle 2 in Table 1) with the neutravidin capturing molecule was used to analyze the biotin target immobilizing matrix. 1 mg of neutravidin or the GST gold particle was suspended in 100 μL of PBS solution, and 10 μL of the suspension was added to the biotin or GSH target immobilizing matrix, and kept for 5 minutes. The, the target immobilizing matrix was washed with PBS and distilled water, dried with nitrogen gas, and then subjected to mass spectrometry.

Figure 6:
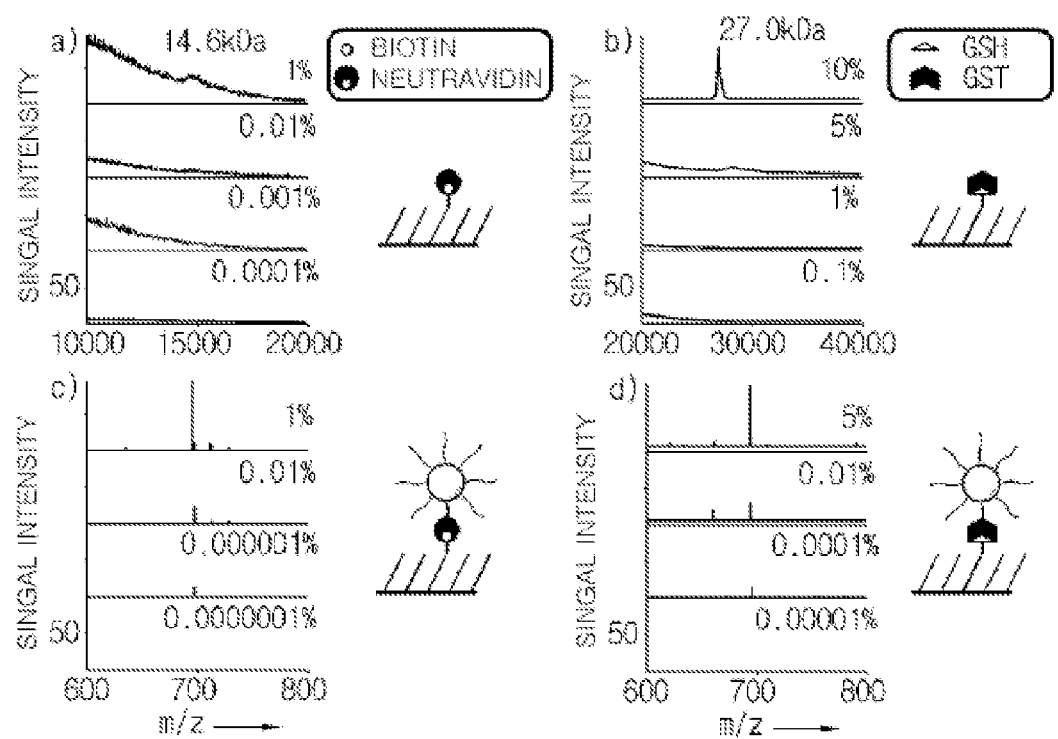
FIG. 6 is a mass spectrometric spectrum graph showing that AM-mass tag molecules are used to form SAMs in a procedure of forming a target immobilizing matrix on which a glutathione target molecule is immobilized.

FIG. 6 is a mass spectrometry spectrum graph showing these mass spectrometric results.

FIGS. 6(A) and 6(C) show the experiment results of a biotin target immobilizing matrix, and FIGS. 6(B) and 6(D) show the experiment results of a glutathione (GSH) target immobilizing matrix. In the spectrum graph as shown in FIG. 6, the percentage (%) in the graph represents a fixed density of the target molecule present in the entire surface of the target immobilizing matrix. Here, the fixed density may be set by adjusting a mixing ratio between the mass tags in the step (i.e., Substep ② of Example 3) of adjusting a volume ratio of AM-mass tag 1 and AM-mass tag 3 to which the target molecule is bound in the preparation of the target immobilizing matrix in Example 3.

FIG. 6(A) shows the mass spectrum results obtained by directly binding free neutravidin to the biotin target immobilizing matrix without use of the gold particle having the neutravidin capturing molecule and subjecting the biotin target immobilizing matrix to conventional MALDI-TOF mass spectrometry. The mass spectrometric signals (14.6 kDa) of the neutravidin protein was observed at a fixed biotin density of 1%, but was not observed at a fixed biotin density of less than 1%. Therefore, it was revealed that a fixed density of the target molecule was observed as a lower bound of 1% in the direct protein assay without use of the gold particle according to one exemplary embodiment of the present invention. In the experiment as shown in FIG. 6(C), the gold particle (gold particles 2 in Table 1) according to one exemplary embodiment of the present invention was used to undergo matrix-free laser desorption ionization-TOF mass spectrometry. As a result, it was seen that the disulfide bond of AM-mass tag 1 derived from the surface of the gold particle was observed as a signal of m/z=693.2 with a low fixed density of 10-6% in experiment as shown in FIG. 7(C), which clearly indicates that the signals are amplified in a very effective manner.

The analysis results on the glutathione (GSH) target immobilizing matrix were similar to those of the biotin target immobilizing matrix. FIG. 6(B) shows the MALDI-TOF results on the glutathione target immobilizing matrix using glutathione-S-transferase (GST, 27.0 kDa). When the GSH target molecule was immobilized on at least 5% of the surface of the support, it was revealed that the GST mass spectrometric signals were observed. Also, it was revealed that the secondary signals (m/z=693.2, disulfide bond of AM-mass tag 1 similarly to FIG. 6(C)) of the signal generators according to the present invention were observed in a fixed density of 10-4%, as shown in FIG. 6(D) where the gold particle (gold particle in Table 1) of the present invention was subjected to the matrix-free laser desorption ionization mass spectrometry.

Example 5

Specificity of Signal Generation: Generation Non-Specific Signal

The principle of the present invention was proven by one exemplary embodiment with reference to Example 4 and FIG. 6. In order to confirm that it is not true that a signal of m/z=693.2 shown in FIG. 6 was observed since the capturing molecule non-specifically binds to the target molecule or since the signal generators were detached from the target immobilizing matrix or the gold particle regardless of the binding of the capturing molecule to the target molecule, the present inventors performed a control experiment, as follows.

Figure 7:
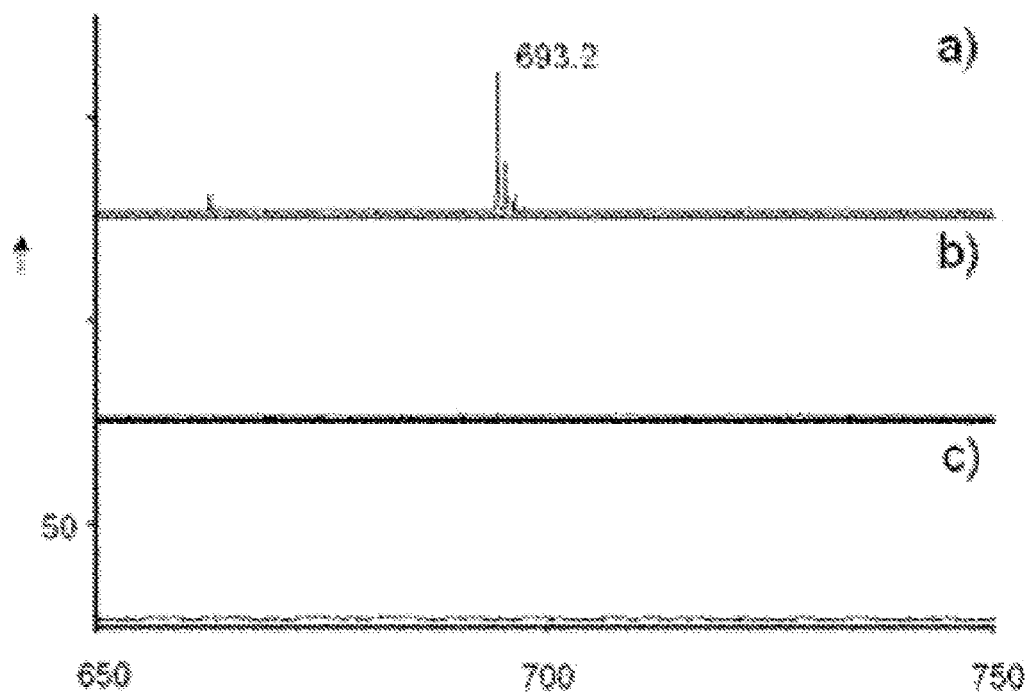
FIG. 7 shows a control experiment performed to demonstrate the generation of specific mass spectrometric signals of the AM-mass tags according to one exemplary embodiment of the present invention.

FIG. 7(A) shows the results of a positive control experiment performed by allowing the gold particle having the neutravidin capturing molecule to react to the biotin target immobilizing matrix prepared in Example 3. In this case, a disulfide signal (m/z=693.2) of AM-mass tag 1 was clearly observed. FIG. 7(B) shows the experimental results obtained by allowing the gold particle (gold particle 5 in Table 1) having the myoglobin capturing molecule to react to the biotin target immobilizing matrix. The signal generators shown in FIGS. 7(A) and 7(B) were composed of the same AM-mass tag 1, but no signal of m/z=693.2 was observed in FIG. 7(B) where the capturing molecule has no specificity to the target molecule. FIG. 7(C) shows the mass spectrometric results obtained by allowing the neutravidin gold particle to react to the target molecule-free target immobilizing matrix. The target immobilizing matrix used in FIG. 7(C) was the target immobilizing matrix prepared in Substep ④ of Example 3, that is, a target immobilizing matrix in which SAM is formed of AM-mass tags 1 and 3. From the results of FIG. 7, it was revealed that the secondary signals according to the present invention were observed only when the capturing molecule and the target molecule were present in the reaction mixture and there is a specific binding property between the capturing molecule and the target molecule.

Figure 8:
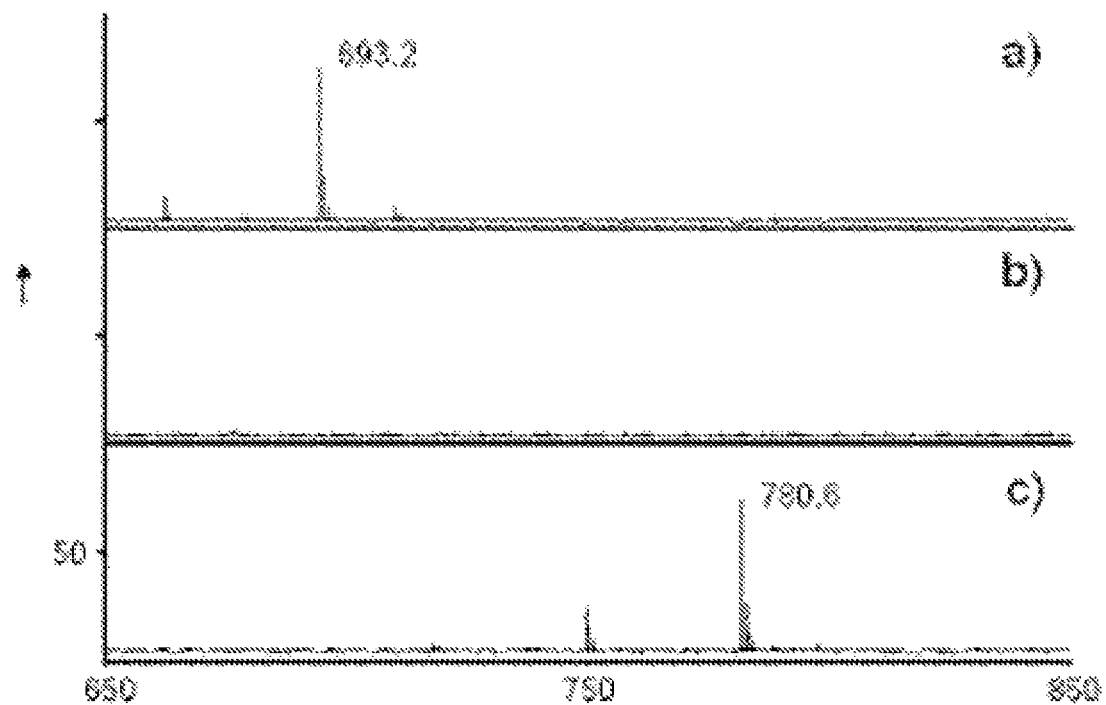
FIG. 8 shows a control experiment performed to demonstrate the generation of specific mass spectrometric signals of the AM-mass tags according to one exemplary embodiment of the present invention.

Since the AM-mass tags were present in both of the target immobilizing matrix and the gold particle as shown in FIG. 7, it is difficult to completely rule out the possibility that the signal of m/z=693.2 is not derived from the target immobilizing matrix. In order to confirm that it is true that the signal was observed in the experiment as shown in FIG. 8 since the signal generators were detached from only the gold particle, the present inventors performed a control experiment, as follows. That is to say, AM-mass tag 1 was used as the SAM component of the target immobilizing matrix and AM-mass tag 5 of FIG. 2 was used as the signal generators of the gold particle to determine whether the signal was derived from AM-mass tag 1 or 5.

FIG. 8(A) shows the results of a positive control experiment performed by subjecting the SAM gold plate, which has only a self assembled monolayer of AM-mass tag 1 formed in the surface thereof, to conventional MALDI-TOF mass spectrometry (See Example 8 using DHB as a matrix). When the target molecule and the gold particle were not used, a disulfide signal of AM-mass tag 1 was not observed in the MALDI-TOF mass spectrum. FIG. 8(B) shows the experimental results obtained by subjecting the same SAM gold plate without addition of the gold particle and formation of the matrix to laser desorption ionization mass spectrometry. In this case, it was seen that the disulfide signal (m/z=693.2) of AM-mass tag 1 derived from the SAM gold plate was not observed. FIG. 8(C) shows the experimental results obtained by adding the gold particle having signal generators of AM-mass tag 5 to the same SAM gold plate and subjecting the SAM gold plate to laser desorption ionization mass spectrometry without formation of the matrix. In the mass spectrum graph shown in FIG. 8(C), a disulfide signal (m/z=780.6) of the gold particle-derived AM-mass tag 5 was observed, but a signal of m/z=693.2 derived from the SAM gold plate was not observed.

As described above, the AM-mass tags according to one exemplary embodiment of the present invention may be used to perform the laser desorption ionization mass spectrometry without any formation of the matrix, and to avoid the generation/detection of non-specific signals from the target immobilizing matrix, which renders it possible to detect highly specific target molecules. In the mass spectrometry according to one exemplary embodiment of the present invention, it was seen that the mass spectrometric signals were derived from the gold particle rather than the target immobilizing matrix.

Example 6

Preparation of Target Immobilizing Matrix Having Antibody Capturing Molecule

In order to analyze the target molecule present in a liquid test sample without immobilization of the target molecule as described in Examples 3 and 4, a target immobilizing matrix which might be applied to gold particles 3 and 4 listed in Table 1 was prepared. Regardless of the gold particle, the target immobilizing matrix had capturing molecules formed on the surface thereof. In this case, a monoclonal antibody that specifically binds to one common target molecule was used as the capturing molecules of the gold particle and the target immobilizing matrix.

Simply, a gold chip was soaked for 12 hours in a mixed solution prepared by mixing an ethanol solution of AM-mass tag 1 with an ethanol solution of AM-mass tag 2 at a volume ratio of 99:5. The gold chip was washed with absolute ethanol and dried under a nitrogen atmosphere. Then, the gold chip was treated with 7 µL of NHS (20 mg/mL PBS solution) and EDC (20 mg/mL PBS solution) for 2 hours, washed with PBS, and then dried under a nitrogen atmosphere. 10 µL of 3.3 µM PBS solution containing the corresponding monoclonal antibody was added to the gold chip, and incubated for 1 hour. Then, the gold chip was washed with PBS, dried and stored at 4° C. An anti-AFP antibody (corresponding to gold particle 3 in Table 1) or an anti-adiponectin antibody (corresponding to gold particle 4 in Table 1) was used as the monoclonal antibody.

Example 7

Liquid Analysis of Adiponectin and AFP Target Molecule

The target immobilizing matrix prepared in Example 6 and gold particles 3 or 4 of Example 2 were applied to the AFP or adiponectin target molecule in a liquid test sample, respectively. In brief, 5 µL of an AFP or adiponectin antigen was added to the target immobilizing matrix prepared in Example 6. In this case, the final antigen concentration was varied from 1 pM to 1 aM ($=10^{-18}$ M). Within 30 minutes, 10 µL of suspension (10 mg/mL PBS suspension) containing the gold particle with an antibody capturing molecule was added to the target immobilizing matrix, and reacted for 30 minutes. The resulting capturing mixture was washed with PBS and distilled water, dried with nitrogen, and then directly subjected to laser desorption ionization mass spectrometry without any formation of the matrix.

Figure 9:
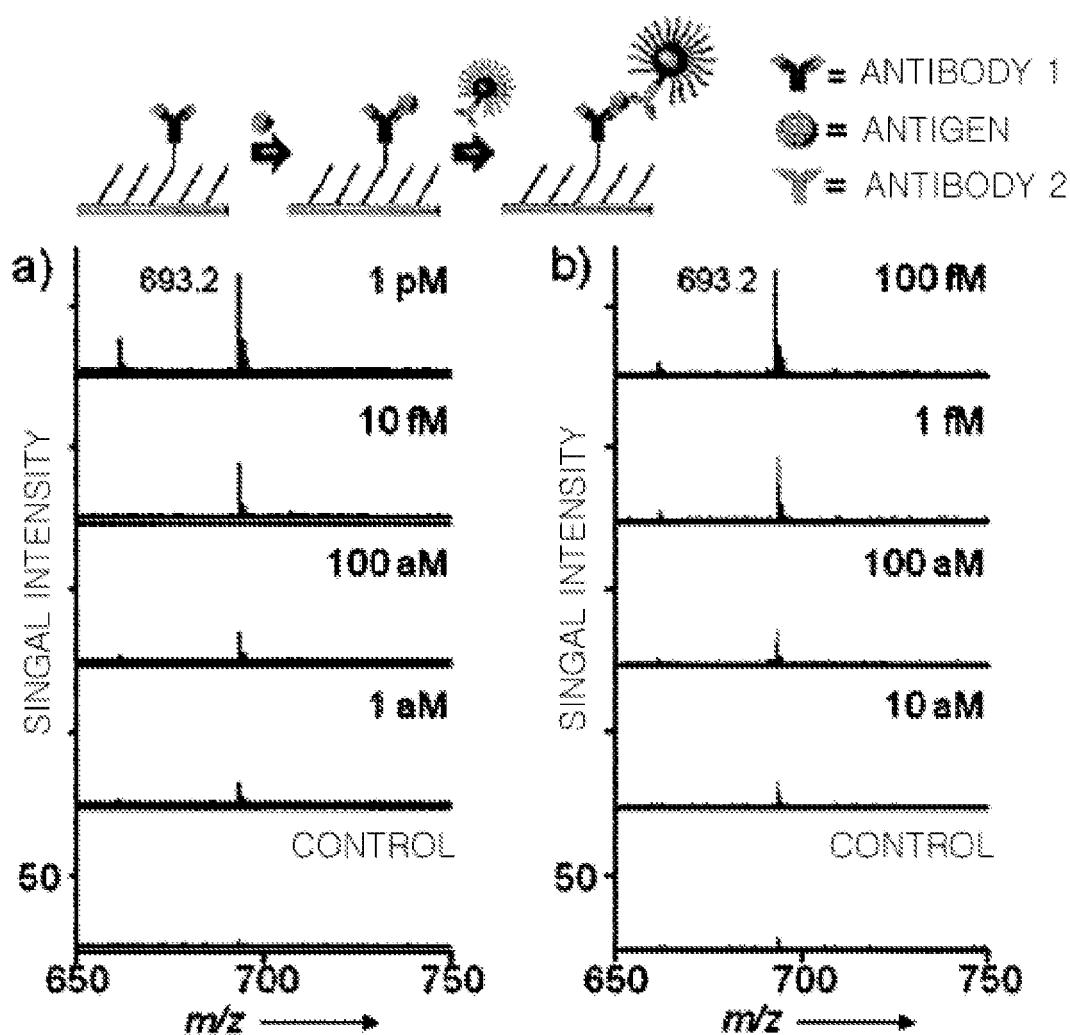
FIG. 9 is a mass spectrum graph showing the results obtained by subjecting an AFP target molecule or an adiponectin target molecule in liquid phase to mass spectrometry.

FIG. 9 shows the mass spectrometric results. FIG. 9(A) shows the mass spectrum results obtained using different monoclonal antibodies against the adiponectin target molecule as the capturing molecules of the gold particle and the target immobilizing matrix, respectively. Since the signal of m/z=693.2 derived from the signal generators of the gold particle was observed at a low concentration (approximately 1 aM) of the test sample as shown in FIG. 9(A), it was seen that the method according to the present invention has a highly sensitive detection property. In the experiment using AFP as shown in FIG. 9(B), it was also seen that method according to the present invention has a minimum detection limit of 10 aM.

As described above, it was revealed from Examples that the signal amplification mass spectrometry according to the present invention has an advantage in that it may be used to specifically detect a trace of the target molecule.

Example 8

Mass Spectrometry Conditions of Target Molecule

An Autoflex™-III MALDI-TOF mass spectrometer (Bruker Daltonics, Germany) was used as the mass spectrometer, and a SmartBeam™ laser was used as an ionization source. All the mass spectrums were obtained by measuring the target molecule 1000 or 500 times at an accelerating voltage of 19 kV and in a positive mode of 50 Hz repeat time.

The capturing mixture to which the target molecule in the test sample has been captured was introduced into a mass spectrometer without any formation of the matrix. The MALDI-TOF mass spectrometry was performed in a Reflectron Positive mode to determine whether a self assembled monolayer of AM-mass tag was formed on the gold particle or the target immobilizing matrix. Here, 2,5-dihydroxybenzoic acid (DHB, 5 mg/mL acetonitrile solution) was used as the matrix. In the experiment performed to determine whether the observed signals are signals of the target molecule protein rather than indirect signals of the AM-mass tags, the MALDI-TOF mass spectrometry was performed in a Linear Positive mode using sinapinic acid (SA, 5 mg/mL acetonitrile solution) as the matrix.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

The invention claimed is:

1. A system for mass spectrometric analysis to detect whether a target molecule is present in a test sample, comprising:

a gold particle for capturing a target molecule and amplifying mass spectrometric signals, the surface of the gold particle being modified with organic molecules, comprising:
- a plurality of signal generators coupled to the surface of the gold particle having a self assembled monolayer formed on the surface thereof;
- at least one linker coupled to the surface of the gold particle; and
- a capturing molecule coupled to the linker to specifically bind or react to a target molecule,
- wherein the signal generators are organic molecules which are released from the gold particle in a mass spectrometric analysis of the gold particle that generate a plurality of organic cations having a different mass weight from the target molecule and
- wherein the signal generators comprise an ether terminus and an alkanethiol portion coupled to the ether terminus and immobilized on the surface of the gold particle; and a target immobilizing matrix for immobilizing the target molecule in the test sample to be analyzed on the surface of a support,
- wherein the target immobilizing matrix is provided with a solid support to immobilize the target molecule in the test sample, which is used to determine the presence of the target molecule, on the surface of the support via a covalent bond or a non-covalent bond,
- wherein the target immobilizing matrix comprises:
  - a self assembled monolayer formed on the surface thereof;
  - at least one linker coupled to the surface of the target immobilizing matrix; and
  - a capturing molecule coupled to the linker to immobilize the target molecule via a covalent bond or a non-covalent bond.

2. The system according to claim 1, wherein the solid support is selected from the group consisting of glass, silicon, metal, semiconductor, and plastic.

3. The system according to claim 1, wherein the target immobilizing matrix is a biochip.

4. The system according to claim 1, wherein the ether terminus comprises at least one ethylene glycol unit.

5. The system according to claim 1, wherein the capturing molecule for the gold particle and the capturing molecule for the target immobilizing matrix are the same or different antibodies that specifically bind to the target molecule.

6. The system according to claim 1, comprising a combination of various kinds of gold particles each having different capturing molecules, and different signal generators.

7. The system according to claim 1, wherein the target molecule is biomolecule.

8. The system according to claim 1, wherein each of the capturing molecules is selected from the group consisting of proteins, peptides, nucleic acids, carbohydrates, lipids, carbohydrate-protein conjugates, lipid-protein conjugates and organic compounds.

9. The system according to claim 8, wherein the capturing molecule is protein, and is bound to the linker via a peptide bond.

10. The system according to claim 1, wherein each of the signal generators has an alkanethiol portion formed at one terminus thereof, the alkanethiol portion being bound to the surface of the gold particle via a gold-sulfur (Au—S) bond, and has an ether portion formed at the other terminus thereof.

11. The system according to claim 10, wherein the ether terminus comprises at least one ethylene glycol unit.

12. The system according to claim 1, wherein the mass spectrometric analysis is the type of matrix-assisted laser desorption ionization-time of flight (MALDI-TOF) mass spectrometry.

* * * * *